United States Patent [19]
Horstmann et al.

[11] Patent Number: 5,230,898
[45] Date of Patent: Jul. 27, 1993

[54] TRANSDERMAL THERAPEUTIC SYSTEM EXHIBITING AN INCREASED ACTIVE SUBSTANCE FLOW AND PROCESS FOR THE PRODUCTION THEREOF

[75] Inventors: Michael Horstmann; Fritz Herrmann, both of Neuwied, Fed. Rep. of Germany

[73] Assignee: LTS Lohmann Therapie-Systeme GmbH & Co. K.G., Neuwied, Fed. Rep. of Germany

[21] Appl. No.: 500,646

[22] Filed: Mar. 28, 1990

[30] Foreign Application Priority Data

Apr. 1, 1989 [DE] Fed. Rep. of Germany ....... 3910543

[51] Int. Cl.$^5$ .......................... A61K 9/70; A61K 9/14; A61K 47/36; A61L 15/42
[52] U.S. Cl. .................................. 424/449; 424/443; 424/445; 424/484; 424/486
[58] Field of Search ............... 424/449, 443, 445, 484, 424/486, 488, 489, 490, 473, 497, 498; 514/772.2, 772.3, 772.4, 777

[56] References Cited

U.S. PATENT DOCUMENTS

| | | | |
|---|---|---|---|
| 3,921,636 | 11/1975 | Zaffaroni | 424/486 |
| 3,993,072 | 11/1976 | Zaffaroni | 424/423 |
| 4,314,557 | 2/1982 | Chandrasekaran | 424/449 |
| 4,781,924 | 11/1988 | Lee et al. | 424/486 |
| 4,834,978 | 5/1989 | Nuwayser | 424/449 |
| 4,837,027 | 6/1989 | Lee et al. | 424/449 |
| 4,942,037 | 7/1990 | Bondi et al. | 424/449 |

FOREIGN PATENT DOCUMENTS 0040861 1/1980 European Pat. Off.
0196769 2/1986 European Pat. Off.
1361289 7/1974 United Kingdom.

OTHER PUBLICATIONS

Yie W. Chien, "Development of Transdermal Drug Delivery Systems," in Drug Development and Industrial Pharmacy, 1987, pp. 589-651.

Primary Examiner—Thurman K. Page
Assistant Examiner—Carlos Azpuru
Attorney, Agent, or Firm—Sprung Horn Kramer & Woods

[57] ABSTRACT

A transdermal therapeutic system exhibiting layered structure consists of a backing layer which is impermeable to active substances, a matrix having water-insoluble basic material and islands (inclusions) divided therein, and a layer controlling the access of cutaneous liquid by means of which the matrix is activatable. Process for the production are described.

13 Claims, 1 Drawing Sheet

TRANSDERMAL THERAPEUTIC SYSTEM EXHIBITING AN INCREASED ACTIVE SUBSTANCE FLOW AND PROCESS FOR THE PRODUCTION THEREOF

The present invention relates to a transdermal therapeutic system exhibiting a layered structure, consisting of a backing layer which is substantially impermeable to active substances, a matrix comprising the active substance and being activatable, and a layer controlling the access of cutaneous liquid; the present invention further relates to a process for the production of such a system.

Transdermal therapeutic systems are self-adhesive galenic preparations to be applied to the skin having a fixed application surface; these preparations release a pharmaceutical to the human or animal body in a controlled way with respect to time and quantity. Such systems, e.g., have been described by Y.W. Chien, Drug Dev. Ind.Pharm. 13, 589–651 (1987), and have become well established in therapy for many years.

Usual constructions of transdermal systems already used in practice are:

a) composition comprising an impermeable carrier and a second layer simultaneously serving as drug-reservoir, pressure-sensitive adhesive and controlling unit, b) composition comprising a carrier, drug-reservoir, controlling unit, and adhesive layer in spatial separation, c) composition comprising a carrier and a drug-containing, multi-layer matrix, whereby the active substance concentration becomes lower from layer to layer towards the skin, d) composition comprising a carrier and a matrix, whereby the release is controlled by drug-containing microcapsules dispersed through the matrix.

The therapeutic progress of such systems compared with traditional application forms is the fact that the active substance is not released to the body intermittently, as is the case, e.g., when taking tablets, but continuously.

In this manner, the duration of efficiency of the pharmaceutical is extended on the one hand, and on the other hand, side effects are widely prevented by avoiding unnecessary blood level peaks.

However, since the skin does not exhibit sufficient permeability to all suitable pharmaceuticals, only few active substances may be employed in transdermal therapeutic systems of common composition. Thus various tests have been conducted aiming at an increase of the natural permeability of the skin.

Such a possibility is the use of so-called "penetration intensifiers". These are substances which achieve a considerable increase of active substance flow by chemicophysical interaction with the micro-structure of the skin. Many of these substances, however, have a toxic effect to the skin and create irritations. Furthermore, the effect of these resorption promoters does not always occur rapidly enough, so that the effect is difficult to control.

Another possibility is the use of physical principles, such as, e.g., iontophoresis. These processes, however, require comparatively expensive additional devices within the transdermal therapeutic system, and thus this form of therapy is generally rendered uneconomic.

A basically different way to increase the permeability of the skin is to increase the thermodynamic activity of the active substance. Corresponding tests aimed at an increase of active substance concentration taking effect from the outside, in order to increase the permeation. These efforts were limited by the fact that, in general, the concentration of an active substance cannot be increased beyond the saturation solubility; on the other hand it did not prove to be successful to use galenic basic materials exhibiting higher solubility for the active substance in transdermal therapeutic systems, since here the connection between distribution coefficient and solubility according to the Nernst distributuion law takes effect.

Temporarily so-called supersaturated states may arise in which the dissolved active substance concentration is above the saturation concentration, e.g., when cooling a saturated solution, or when redissolving an embedded active substance in a water-soluble polymer, as is described, e.g., by Merkle, Pharm. Ind. 42, 1009–1018 (1980).

Depending on the degree of supersaturation and the viscosity of the surrounding medium this state may last from a few seconds to up to several years. In the case of adhesive polymer matrices which have a relatively low viscosity this state, in general, remains stable for a few weeks at most. The duration of the stable condition is impaired, amongst others, by the possibility that the present interfaces may act as crystallization nuclei.

The production of storable transdermal therapeutic systems comprising an supersaturated solution of the active substance therefore encouter greatest difficulties.

EP-A-0 186 019 describes that the addition of water-swellable polymers to a solution of the active substance in a basic polymeric material remarkably increases the release velocity of a transdermal therapeutic system manufactured from this mass.

In the process described, the active substance and water-swellable additive are added to the formulation of the basic mass, which is prepared in lipophilic solvents, in one process step so that an intended enrichment of the active substance in the hydrophilic domains is not possible. Addition of cutaneous liquid is effected in an uncontrolled manner.

If the supersaturated condition is created only when the pharmaceutical is already present on the skin, stability problems with respect to storage naturally arise. Coldman et al (J. Pharm. Sci. 58, 1098–1102 (1969) describe a resorption intensification of fluocinolone by solution in a mixture of volatile and non-volatile solvents, whereby on evaporation of the highly volatile component an supersaturated solution results which leads to a higher skin penetration. Kondo et al (J. Pharmacobio. Dyn. 10, 662-668 (1987) confirmed these effects with the use of nifedipine.

Accordingly, it is the object of the present invention to provide a transdermal therapeutic system exhibiting an increased active substance flow and a formulation which is stable in storage; a further object is to provide a process for the production of such a system.

According to the present invention this object was achieved by providing a transdermal therapeutic system exhibiting a layer construction consisting of a backing layer (11) which is substantially impermeable to active substances, a matrix (12) containing the active stubstance and being activatable, and a layer (13) controlling the access of cutaneous liquid. This system is characterized in that the matrix consists of a basic material (15) which is permeable to water-vapour but substantially water-insoluble and mainly free of active substance. Said basic material comprises islands (14) distributed therein, which inclusions consist of a solid pharmaceutical solution in a basic material being water-soluble or water-swellable; furthermore the system is characterized in that the matrix is activatable by cutaneous liquid whereby a controlled access of skin moisture into the matrix (12) is effected, and that the islands (14) absorb moisture so that a system-controlled, intended supersaturation with active substance takes place which results in an increased release of pharmaceutical. The object of the present invention was further achieved by a process for the production of the therapeutic system wherein the islands (14, 24) are obtained by spray drying a solution of the active substance and the moisture absorbing basic material in a suitable solvent by drying as thin layer a solution of the active substance and the moisture absorbing basic material in a suitable solvent, and by subsequent milling or by precipitation from a solution of the active substance and the moisture absorbing basic material by means of a suitable precipitation agent in which the moisture absorbing basic material is substantially insoluble. Loading of the islands (14, 24) with active substance is carried out by means of solid-liquid absorption in a suspension of unloaded islands in a suitable solvent comprising the active substance in dissolved form.

Advantageously, the matrix (12, 22) or the layer controlling the access of cutaneous liquid (13, 23) is applied to a carrier, which has been rendered dehesive, in a solution or suspension in a suitable solvent, and the solvent is subsequently removed by drying. The cutaneous liquid access controlling layer (13, 23) is liquefied by application of heat, and applied in this state to a dehesive carrier, and the matrix (12, 22), the cutaneous liquid access controlling layer (13, 23), and backing layer (11, 21) are continuously combined by application of pressure and/or temperature. The matrix (22) is formed by separate manufacture of two identical layers of basic material (25), optionally having a different layer thickness, sprinkling the islands (24) on one of the two layers, and subsequent application of the second layer of basic material (25) under application of pressure and/or temperature.

Suitable active substances can be selected from the active substance groups consisting of parasympathicolytics (e.g., scopolamine, atropine, benactyzine), cholinergics (e.g., physostigmine, nicotine), neuroleptics (e.g., chlorpromazine, haloperidol), monoamine oxidase inhibitors (e.g., tranylcypromine, selegiline), sympathomimetics (e.g., ephedrine, D-norpseudoephedrine, salbutamol, fenfluramine), adrenergic blockers and anticympathotonics (e.g., propanolol, timolol, bupranolol, clonidine, dihydroergotamine, naphazoline), anxiolytics (e.g., diazepam, triazolam), local anesthetics (e.g., lidocaine), central analgesics (e.g., fentanyl, sufentanil), antirheumatics (e.g., indomethacin, piroxicam, lornoxicam), coronary pharmaceuticals (e.g., glycerol trinitrate, isosorbide dinitrate), estrogens, progestins, and androgens, antihistamines (e.g., diphenhydramine, clemastine, terfenadine), prostaglandin derivatives, vitamins (e.g., vitamin E, cholecalciferol), and antitumor agents. Furthermore, other active substances are suitable for the purpose according to the present invention, if they exhibit a therapeutic daily dosage of less than 50 mg and are soluble both in water and in organic solvents.

As components in the basic material (15, 25) of the matrix (12, 22) polymers may be used, e.g., polyisobutylene, ester of polyvinyl alcohol, polyacrylic and polymethacrylic acid esters, natural rubber, polymers of styrene, isoprene, and styrene-butadiene or silicone polymers, resin components, such as, saturated and unsaturated hydrocarbon resins, derivatives of abietyl alcohol and of $\beta$-pinene, plasticizers, such as phthalic acid esters, triglycerides and fatty acids, as well as a series of other substances known to those skilled in the art.

A variety of pharmaceutical auxiliaries which are swellable in water, such as, e.g., polyvinyl pyrrolidone, polyacrylic acid, polyvinyl alcohol, cellulose and its derivatives, naturally occurring slime formers, e.g., agar (agar), guar gum, and gum arabic, but as well inorganic materials, such as kaolin or bentonite are suitable components for the base material of the islands (14, 24).

In the case of the layer on the skin side (13, 23), which controls the moisture access to the matrix, the choice of the thickness and the materials used are of particular importance, since both factors together considerably determine the course of swelling of the islands (14, 24), which is caused by moisture absorption, and thus determine the degree of supersaturation. If the access of cutaneous liquid takes place too rapidly, the supersaturation within the islands (inclusions) is effected too fast and too high, so that precipitation of the active substance and thus falling-down of the release rate to the saturation-flow-level would result. If the moisture diffuses too slowly into the matrix, the supersaturated state is created too late, and the release potential within the islands is not utilized in an optimal manner.

Suitable basic polymers for moisture access controlling layer (13, 23), e.g., are polyacrylic acid ester and polymethacrylic acid ester, polyvinyl alcohol and the esters thereof, polyisobutylene, or polyethylene. It is not necessary that the moisture access is controlled by the diffusivity of the material used—it is possible, too, that the access is controlled by the porosity of the material used. The moisture access can also be controlled by the addition of inert, powdery charges, e.g., talcum, quartz powder, activated carbon, etc.

By way of selective choice of the basic polymer or by suitable additives, e.g., resins and plasticizers, the moisture access controlling layer (13, 23) can be rendered pressure-sensitive adhesive, according to a particular embodiment of the present invention.

The process for the production of such systems can be carried out in different ways.

In the manufacture of the islands (14, 24), complete dissolution of the active substance in the basic material must be taken care of, so that no crystal nuclei are brought into the formulation of the pharmaceutical.

Thus preferred processes are those where common dissolution of active substance and auxiliaries in adequate solvents and subsequent drying takes place.

In this connection, the process of spray drying is particularly preferred, in which a drying process and a size-reduction process are combined so that the desired particles are obtained in one process step. However, it is possible, too, to spread the solution of active substance and auxiliary agents on metal rolls or dehesive carriers, to dry the solution as such a thin layer, and subsequently subject it to dry-milling according to processes known to the man skilled in the art.

In another suitable alternative, a precipitation agent is added to the solution of active substance and auxiliaries, said precipitation agent leading to a particulate precipitation of at least part of the auxiliaries. In this process dissolved active substance is retained in the particles of the basic materials. The particles are dried subsequent to separation of the particles by filtration, classifying, wet screening, or another process suitable for this purpose.

If the basic material is present in an adequate grain size distribution even prior to the production, it is possible, too, to disperse these particles in a solution of the active substance, and thus achieve a saturation of the basic material with active substance by absorption. In this case, too, a drying process (e.g., tray drying or fluid-bed drying) has to follow the separation process, e.g., filtration, screening, classifying, etc., in order to create islands (14, 24) according to the present invention.

The grain size of the islands should always be smaller than the intended thickness of matrix (12, 22). Considerably smaller grain sizes are preferred, since separation into as much individual compartments as possible can effectively prevent the development of possible crystallizations during wearing of the system.

For this reason particle sizes of maximal 5 to 20 $\mu m$ are preferred, particularly preferred are those below 5 $\mu m$.

The active substance portion of the island base material typically is 5 to 50% below the saturation solubility of the active substance in the dry basic material. In case of particularly brittle, glass-like basic materials, the saturation solubility may even be exceeded by up to approximately 300%, since in the case of these basic materials crystallization occurs at an extreme delay.

In order to manufacture the matrix layer, the basic material can be dissolved in a solvent, in which the basic material of the islands is insoluble, and the particles dispersed therein. Such a suspension, preferably in a coating device, is applied on a carrier which has been rendered dehesive and on which the matrix layer is solidified, e.g., by drying in hot-air stream. Solvents suitable for this purpose are mixtures of benzene having adequate boiling ranges, toluene, methylene chloride, and many other lipiphilic, readily volatile substances which do not considerably influence the structure of the hydrophilic islands.

In case of sufficiently temperature-resistant active substances solvent-free processes are particularly suitable. For example, the basic material (15) may be brought into a spreadable condition by the application of shear force and heat, the necessary amount of islands may be kneaded or mixed in, and the mass, after application to a dehesive carrier, may then be cooled.

Both the solvent process and the melting process are suitable processes for the production of the layer controlling the access of cutaneous liquid (13, 23).

According to a particular embodiment of the present invention at first two layers of basic material are produced according to one of the beforementioned processes—however, free of islands first.

Both layers consist of the same material, however, do not necessarily exhibit the same thickness. The spreadable, particulate islands (always having the same surface load) are sprinkled homogeneously. Subsequently, the second part of the matrix layer is laminated thereon by rolling under pressure. If necessary, the process can be accelerated by the application of heat.

The portion of island material (basic material and active substance) to the matrix mainly depends on the amount of active substance in the basic material of the islands, the thickness of the matrix layer, and the required active substance load of the transdermal therapeutic system per area unit. In general, an amount between 0.5 and 70%, preferably between 5 and 40% is aimed at.

The combination of matrix and the cutaneous liquid access controlling layer suitably is carried out in a lamination device in which both layers can be brought to continuous adhesion by the application of pressure. If necessary, heat may be applied in order to intensify and accelerate this process.

The finished system may be covered with an adhesive cover.

Cutting or punching into desired geometric forms and sizes in the first place is carried out according to the therapeutic requirements, e.g., intended daily dosage, permeability of the skin, and degree of flexion of the skin area to be covered.

Particularly suitable as packing are multi-layered primary packings serving as barrier to water vapour, e.g., made of a polyethylene copolymer/aluminum/paper-composite.

DESCRIPTION OF THE DRAWINGS

The composition of the transdermal therapeutic system according to the present invention is illustrated by FIGS. 1 and 2.

Meanings.

(12) matrix with islands (inclusions);

(13) layer facing the skin and controlling the access of cutaneous liquid;

(14) active substance containing islands.

Figure 1:
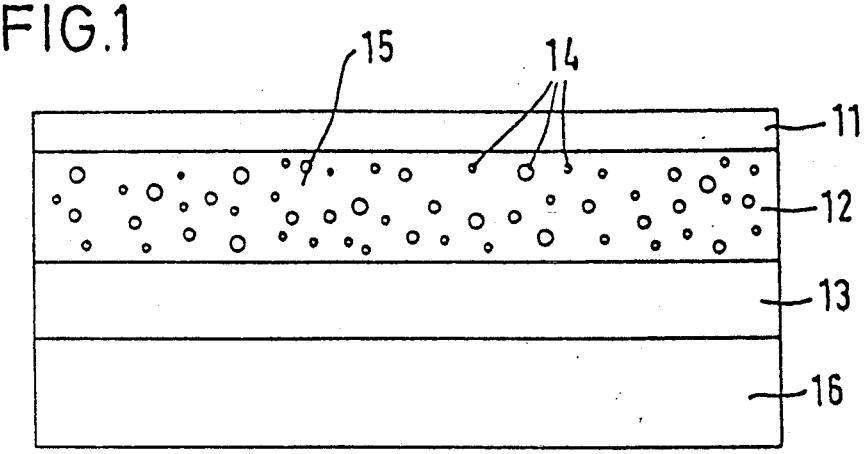
FIG. 1: (11) backing layer.
Figure 2:
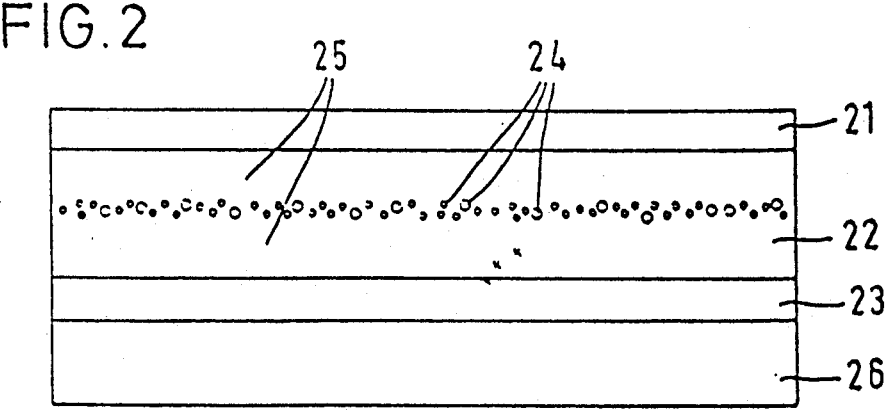

(15) basic material of matrix;

(16) removable protective layer;

FIG. 2: (21) backing layer;

(22) matrix comprising arrangement of islands parallel to the releasing surface;

(23) layer facing the skin and controlling the access of cutaneous liquid;

(24) active substance containing islands, positioned in a plane;

(25) basic material of matrix, combined of two layers;

(26) removable protective layer.

The invention is further illustrated but not limited by the following examples:

EXAMPLE 1:

250 mg haloperidol are completely dissolved in 25 g ethyl acetate in a 100-ml-beaker provided with magnetic stirring rod. Subsequently, 5 g cross-linked polyvinyl pyrrolidone (maximum grain size 150 micro meters) are added slowly, and the suspension is stirred for 2 hours at 22° C. The swollen particles together with the adhering solvent are dried for one hour as thin layer on a siliconized polyester foil at 80° C. in a fresh-air-drying oven.

4.3 g of the thus obtained powdery embedding (comprising 205 mg haloperidol and 4095 mg polyvinyl pyrrolidone)

10.0 g heat-vulcanizable dimethylpolysiloxane and 3.2 g benzine are unified under slow stirring until an optically homogeneous mass results, thereby avoiding incorporation of air-bubbles. The mass is coated by means of a film applicator (gap 300 micro meters) on a polyester carrier of 25 $\mu m$ thickness, cross-linked for half an hour at a temperature of 80° C. and simultaneously dried. The polymerized layer is subsequently again covered with a commercially available silicone adhesive mass by means of a film applicator (gap 100 micro meters). The final drying is effected unclosed at room temperature within 30 minutes, and subsequently in the drying oven at 50° C. for 10 minutes.

EXAMPLE 2:

(Comparison Example to Example 1)

0.205 g haloperidol
4.095 g cross-linked polyvinyl pyrrolidone
10.0 g heat-vulcanizable dimethylpolysiloxane and
3.2 g benzine are unified under slow stirring until an optically homogeneous mass without air-bubbles results. Further processing (coating, cross-linking, covering with silicone adhesive mass, drying) is conducted as described in example 1.

EXAMPLE 3:

Determination of Skin Permeation

Circular pieces of the formulations according to examples 1 and 2 (surface 2.54 cm²) are bonded centrally on a piece of excised hairless mice skin. The skin pieces are fit in a permeation apparatus, the basic construction of which is described by Kondo et al, J. Pharmacobio.-Dyn. 10, 662–668 (1987). As acceptor solution the cell used contained a phosphate buffer of a pH-value of 5.5 and was thermostatted to 37.0° C. over a tempering jacket.

The determination of the released haloperidol amount was carried out by high pressure liquid chromatography (reverse phase, detection UV at 242 nm). The following results were obtained

| Example | amount of haloperidol (μg) (on 2.54 cm²) released within 24 hours |
|---------|-------------------------------------------------------------------|
| 1       | 68                                                                |
| 2       | 36                                                                |

By the composition according to the present invention according to example 1 a considerably higher skin permeation is achieved compared to that according to comparison example 2.

It is understood that the specification and examples are illustrative but not limitative of the present invention and that other embodiments within the spirit and scope of the invention will suggest themselves to those skilled in the art.

What is claimed is:

1. A transdermal therapeutic system exhibiting a layered structure and comprising a backing layer (11) which is substantially impermeable to active substances, a matrix (12) containing the active substance in an activatable form, and a layer (13) controlling the access of cutaneous liquid, the improvement wherein the matrix (12) comprises a material (15) which is permeable to water vapour, but substantially water-insoluble, in which islands (14) are distributed which consist of a solid solution of pharmaceutical in a water-soluble or water-swellable basic material, the proportion of islands (14) to the mass of the matrix layer (12) lying between 0.5 and 70%, the matrix being activatable by cutaneous liquid.

2. The transdermal therapeutic system according to claim 1, characterized in that the portion of islands (14) to the mass of the matrix layer (12) lies between 5 and 40%.

3. The transdermal therapeutic system according to claim 1, characterized in that the particle size of the islands (14) amounts to 5 to 20 μm.

4. The transdermal therapeutic system according to claim 1, characterized in that the islands (14, 24) within the basic material (15, 25) are positioned in a plane parallel to the releasing surface.

5. The transdermal therapeutic system according to claim 1, characterized in that the basic material of the water-absorbing islands (14, 24) consists of polyvinyl alcohol, polyvinyl pyrrolidone, copolymers of polymethacrylic acid, polysaccharides, polyethylene glycol, and homogeneous mixtures of these substances.

6. The transdermal therapeutic system according to claim 1, characterized in that an active substance selected from the group consisting of antihistamines, antirheumatics, opioids, anticholinergics. antisympathotonics, steroid hormones, prostaglandins, neuroleptics, and amphetamine derivatives is used in the islands (14, 24).

7. The transdermal theraputic system according to claim 1, characterized in that the cutaneous liquid access controlling layer (13, 23) exhibits pressure-sensitive adhesive properties.

8. The transdermal therapeutic system according to claim 1, characterized in that the cutaneous liquid access controlling layer (13, 23) consists of a mixture of one or more components of polyisobutylene, aliphatic hydrocarbon resins, esters of polyacrylic acid, and silicone polymers.

9. The transdermal therapeutic system according to claim 1, characterized in that the cutaneous liquid access controlling layer (13, 23), the matrix (12, 22), or both of them comprise one or more additives which increase the permeability of the skin to the active substance.

10. The transdermal therapeutic system according to claim 1, characterized in that the layer (13, 23) controlling the access of cutaneous liquid is covered with a removable protective layer (16, 26) during storage.

11. The transdermal therapeutic system according to claim 1, characterized in that the water-insoluble basic material (15, 25) of matrix (12, 22) substantially consists of one or more components or polyisobutylene, natural or synthetic hydrocarbon resins, styrene, butadiene copolymers, polyacrylic acid esters, esters of polyvinyl alcohol, and silicone polymers.

12. The transdermal therapeutic system according to claim 8, characterized in that the cutaneous liquid access controlling layer (13, 23) consists of a mixture of one or more components of polyisobutylene, aliphatic hydrocarbon resins, esters of polyacrylic acid, and silicone polymers, and additives.

13. The transdermal therapeutic system according to claim 12, wherein the additives are resins or plasticizers.

* * * * *

UNITED STATES PATENT AND TRADEMARK OFFICE
CERTIFICATE OF CORRECTION

PATENT NO. : 5,230,898

DATED : July 27, 1993

INVENTOR(S) : Horstmann, et al.

It is certified that error appears in the above-identified patent and that said Letters Patent is hereby corrected as shown below:

Col. 7, line 52    Delete " A " and substitute -- In a --

Signed and Sealed this

Seventeenth Day of January, 1995

Attest:

BRUCE LEHMAN

Attesting Officer

Commissioner of Patents and Trademarks